(12) United States Patent
Fang et al.

(10) Patent No.: US 11,795,490 B2
(45) Date of Patent: Oct. 24, 2023

(54) APPARATUS, METHOD AND SYSTEM FOR SURFICIAL MOLD MONITOR BASED ON WEAK ELECTRICAL SIGNALS

(71) Applicant: Guangzhou University, Guangzhou (CN)

(72) Inventors: Zhaosong Fang, Guangzhou (CN); Zhangyi Xie, Guangzhou (CN); Zhimin Zheng, Guangzhou (CN); Tao Wen, Guangzhou (CN)

(73) Assignee: GUANGZHOU UNIVERSITY, Guangzhou (CN)

( * ) Notice: Subject to any disclaimer, the term of this patent is extended or adjusted under 35 U.S.C. 154(b) by 0 days.

(21) Appl. No.: 17/343,733

(22) Filed: Jun. 10, 2021

(65) Prior Publication Data

US 2022/0127656 A1    Apr. 28, 2022

(30) Foreign Application Priority Data

Oct. 22, 2020 (CN) .......................... 202011136714.7

(51) Int. Cl.
| | |
|---|---|
| *C12Q 1/04* | (2006.01) |
| *C12N 1/00* | (2006.01) |
| *G01N 27/00* | (2006.01) |
| *G01N 27/416* | (2006.01) |

(52) U.S. Cl.
CPC .................. *C12Q 1/04* (2013.01); *C12N 1/00* (2013.01); *G01N 27/002* (2013.01); *G01N 27/416* (2013.01); *G01N 27/4161* (2013.01)

(58) Field of Classification Search
CPC .......... C12Q 1/04; B12N 1/00; G01N 27/002; G01N 27/416; G01N 27/4161
See application file for complete search history.

(56) References Cited

U.S. PATENT DOCUMENTS 6,101,886 A * 8/2000 Brenizer ................ B01D 45/08
                                                                    55/308

OTHER PUBLICATIONS

Chen, Po-Cheng, et al. "Ultrasonically enabled neural probes with co-located electrical and mechanical transduction." 2012 IEEE International Ultrasonics Symposium. IEEE, 2012. (Year: 2012).*
Shekar, Siddharth, et al. "A miniaturized multi-clamp CMOS amplifier for intracellular neural recording." Nature electronics 2.8 (2019): 343-350. (Year: 2019).*

(Continued)

*Primary Examiner* — Robert J Eom
(74) *Attorney, Agent, or Firm* — Getech Law LLC; Jun Ye (57) ABSTRACT

Disclosed are apparatus, method and system for monitoring mold based on weak electrical signals. The apparatus comprises a mold collector, a power supply, a trans-impedance amplifier, and an analog-to-digital converter, wherein the mold collector is smeared with a trophoplasm, and a substrate of the mold collector has electrical conductivity, the power supply is used for applying a voltage to the substrate of the mold collector, the trans-impedance amplifier is used for amplifying a weak current generated from the substrate of the mold collector to a voltage signal, and the analog-to-digital converter is used for converting the voltage signal amplified by the trans-impedance amplifier into a digital signal for determining the quantity of molds.

1 Claim, 5 Drawing Sheets

Weak current based mold sensor (56) References Cited

OTHER PUBLICATIONS

Baldassano, Steven, et al. "Cloud computing for seizure detection in implanted neural devices." Journal of neural engineering 16.2 (2019): 026016. (Year: 2019).*

Islam, Tarikul, Shakeb A. Khan, and Sheikh S. Islam. "Sensitivity enhancement of wheatstone bridge circuit for resistance measurement." Sensors & Transducers 6 (2009): 92. (Year: 2009).*

\* cited by examiner

APPARATUS, METHOD AND SYSTEM FOR SURFICIAL MOLD MONITOR BASED ON WEAK ELECTRICAL SIGNALS

TECHNICAL FIELD

This application generally relates to the technical field of smart home, in particular to an apparatus, method and system for monitoring mold based on weak electrical signals.

BACKGROUND

Explanation of Nouns

[Weak electrical signals] The weak electrical signal means an electrical signal with a minimum signal amplitude ($10^{-3}$ or $10^{-6}$ level). In this application, two signal types: micro-current and micro-voltage are included.

[Low Noise Amplifier] The low-noise (operational) amplifier is a universal integrated circuit, that has the characteristics of low input noise and is in particular suitable for amplifying weak signals.

[Analog Signal] The analog signal means an electrical signal with continuous changes, for example, an electrical signal generated by a mold sensor.

[Digital Signal] The digital signal means a signal including a signal mode of two states, usually identified as 0 or 1, used for Boolean logic operation.

With development of smart home, more and more attention is paid to indoor air quality. Indoor mold growth can greatly affect air quality. Some mold growth can be visible to the naked eye and some are difficult to notice. Excessive mold growth without being noticed and cleaned can be unhealthy and sometimes even hazardous. Thus, simple and effective mold detection is the first and most important step of controlling mold growth and spreading.

Typical method of mold detection is to collect samples within affected areas and send to specific laboratories, where mold must be accumulated on a microscopic slide. Mold concentration is determined by experts viewing through microscope. These procedures are quite complex and costly that not only requires special equipment but also expertise of microbiology, and are not continuously or real time sampling. These limitations hinder mold detection from becoming practical and industrialized.

SUMMARY

The embodiments of the present application provide a convenient and accurate apparatus, method and system for monitoring mold based on weak electrical signals. Molds are spread via spores with air flow. The specific geometry of mold collector is proposed to detect the propagation trajectory of mold spreading. The mold spore is very tiny (micrometer level), which is impossible to be seen by naked eyes, while usually small amount of spores in air that attach to any surface are also very difficult to be detected by any means. The mold collector is not only a collecting device for spores to accumulate, but also a pre-amplifier that help grow the spores into molds and multiplies dramatically, thus generating weak but detectable signal for subsequent circuitry to process. The mold sensor is generally a small thin slide (mainly consists of mold collector) that can be attached to any surface exposed to mold spore environment. By virtue of modern integrated circuits, the detecting circuitry can be made in very small physical size and consumes very little power but still very accurate in processing weak signals, making the mold sensor suitable for any surface in any environment, portable with long battery powered working hours, as well as, low cost and high accuracy.

In the first aspect, the application provides an apparatus for monitoring mold based on weak electrical signals, including a mold collector, a power supply, a trans-impedance amplifier and an analog-to-digital converter, wherein the mold collector is smeared with a trophoplasm, and a substrate of the mold collector has electrical conductivity;

the power supply is used for applying a voltage to the substrate of the mold collector, such that the weak current is generated from the substrate of the mold collector;

the trans-impedance amplifier is used for amplifying a weak current generated from the substrate of the mold collector to a voltage signal; and the analog-to-digital converter is used for converting the voltage signal amplified by the trans-impedance amplifier into a digital signal for determining the quantity of molds.

In some embodiments, the mold collector includes a first collecting unit, a second collecting unit, a third collecting unit and a fourth collecting unit;

the trophoplasm is smeared to the first collecting unit, and the first collecting unit is exposed to air; and the second collecting unit, the third collecting unit, and the fourth collecting unit are used closely.

In some embodiments, the trans-impedance amplifier includes a low-noise operational amplifier unit, a resistor and a capacitor.

In a second aspect, the application provides a method for monitoring mold based on weak electrical signals, including:

applying a voltage to a substrate of a mold collector by a power supply, such that a weak current is generated from the substrate of the mold collector;

amplifying the weak current to a voltage signal by a trans-impedance amplifier;

converting the voltage signal into a digital signal by an analog-to-digital converter; and determining the quantity of molds according to the digital signal.

In some embodiments, the step of applying the voltage to the substrate of the mold collector comprising a first collecting unit, a second collecting unit, a third collecting unit and a fourth collecting unit by the power supply such that the weak current is generated from the substrate of the mold collector, including:

smearing a trophoplasm to the first collecting unit, and exposing the first collecting unit to air; and applying a voltage to the first collecting unit; and outputting a weak voltage by the first collecting unit, the second collecting unit, the third collecting unit, and the fourth collecting unit according to the voltage on the first collecting unit.

In some embodiments, amplifying the weak current to the voltage signal by the trans-impedance amplifier includes:

amplifying the weak current to the voltage signal by a low-noise operational amplifying unit, a resistor and a capacitor in the trans-impedance amplifier.

In a third aspect, the application provides a method for monitoring mold, including:

exposing the apparatus for monitoring mold to air, or attaching the apparatus for monitoring mold to an object surface to be detected; and applying a voltage to the apparatus for monitoring mold to obtain the quantity of molds in the air or on the object to be detected.

In some embodiments, the method includes:
sending a warning prompt according to the quantity of molds; and
generating a mold monitoring result according to the quantity of molds, and uploading the mold monitoring result to a cloud.

In a fourth aspect, the present invention provides a system for monitoring mold, including:
a carrier where an object or environment to be detected is located, wherein the carrier comprises a room, a building, or a cavity;
the apparatus for monitoring mold, wherein the apparatus for monitoring mold is used for acquiring mold monitoring data;
the could is used for storing the mold monitoring data; and
a management terminal is used for controlling the apparatus for monitoring mold.

In a fifth aspect, the mold collector use for accumulating mold and specific structure is drawn to detect mold growth from any direction of air flow, including:
Substrate with trophoplasm coated in grooves of vertical and horizontal; and
Voltage sources swapped periodically across vertical and horizontal directions; and
Subsequent detection circuits used (e.g. weak current type or weak voltage type mention in this application) to measure mold quantity by electrical signal intensities; and
Calculate the mold propagation direction by vector superposition principle.

According to the embodiments of the present application, the voltage is applied to the substrate of the mold collector by the power supply, such that the substrate of the mold collector generates a weak current; the weak current is applied to the voltage signal by the trans-impedance amplifier; the voltage signal is converted into the digital signal by the analog-to-digital converter; and the quantity of the molds is determined according to the digital signal. The apparatus, method and system for monitoring mold is real time and accurate.

BRIEF DESCRIPTION OF THE DRAWINGS

In order to describe the technical schemes in the embodiments of the disclosure more clearly, brief introduction on drawings needed to be used in the embodiments will be made below. It is obvious that the drawings described below are merely some embodiments of the disclosure, and those skilled in the technical field further can obtain other drawings according to the drawings without creative efforts.

DETAILED DESCRIPTION

In order to make purposes, technical schemes and advantages of the disclosure clearer, the disclosure is further described in detail below in combination with drawings and embodiments. It should be understood that the specific examples described herein are merely used for explaining the disclosure, instead of limiting the disclosure.

Aiming to solve the problems in the prior art, the embodiments of the present application provide an apparatus for monitoring mold based on weak electrical signals, including a mold collector, a power supply, a trans-impedance amplifier and an analog-to-digital converter, wherein
the mold collector is smeared with a trophoplasm, and a substrate of the mold collector has electrical conductivity;
the power supply is used for applying a voltage to the substrate of the mold collector, such that weak current is generated from the substrate of the mold collector;
the trans-impedance amplifier is used for amplifying a weak current generated from the substrate of the mold collector to a voltage signal; and
the analog-to-digital converter is used for converting the voltage signal amplified by the trans-impedance amplifier into a digital signal for determining the quantity of molds.

Figure 7:
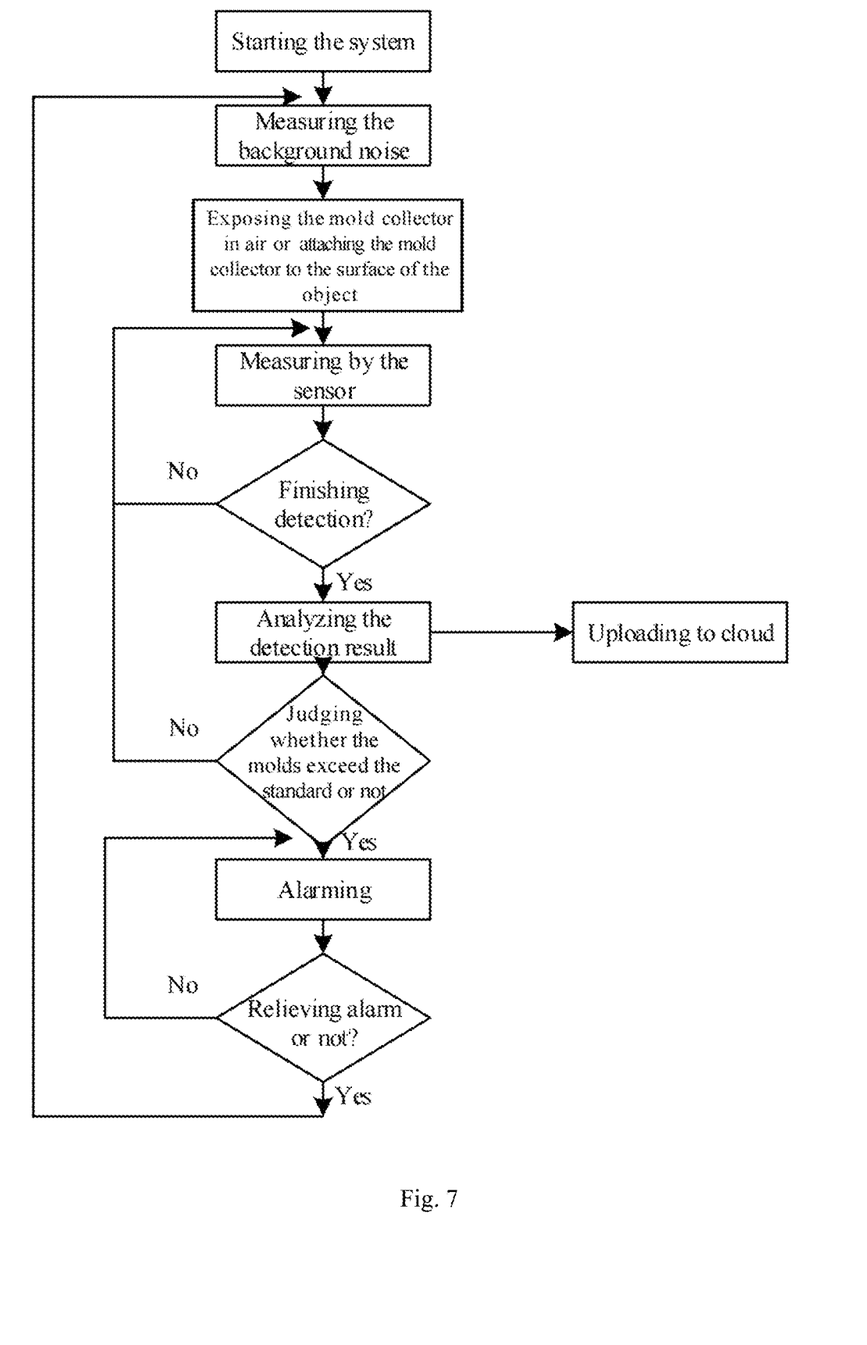
FIG. 7 is a flow diagram of the mold detection method provided by the embodiments of the present application.

With reference to the FIG. 7, the embodiments of the present application provide a method for monitoring mold based on weak electrical signals, including:
applying a voltage to a substrate of a mold collector by a power supply, such that a weak current is generated from the substrate of the mold collector;
amplifying the weak current to a voltage signal by a trans-impedance amplifier;
converting the voltage signal into a digital signal by an analog-to-digital converter; and
determining the quantity of molds according to the digital signal.

In some embodiments, the step of applying the voltage to the substrate of the mold collector comprising a first collecting unit, a second collecting unit, a third collecting unit and a fourth collecting unit by the power supply such that the weak current is generated from the substrate of the mold collector, including:
smearing a trophoplasm to the first collecting unit, and exposing the first collecting unit to air;
applying a voltage to the first collecting unit;
outputting a weak voltage by the first collecting unit, the second collecting unit, the third collecting unit, and the fourth collecting unit according to the voltage on the first collecting unit.

In some embodiments, amplifying the weak current to the voltage signal by the trans-impedance amplifier includes:
amplifying the weak current to the voltage signal by a low-noise operational amplifying unit, a resistor and a capacitor in the trans-impedance amplifier.

The embodiments of the present application further provide a method for monitoring mold, including:
exposing the apparatus for monitoring mold to air, or attaching the apparatus for monitoring mold to an object to be detected; and applying a voltage to the apparatus for monitoring mold to obtain the quantity of molds in the air or on the object to be detected.

In some embodiments, the method includes:

sending a warning prompt according to the quantity of molds; and generating a mold monitoring result according to the quantity of molds, and uploading the mold monitoring result to a cloud.

The embodiments of the present application further provide a system for monitoring mold, including:

a carrier where a to-be-detected object or a to-be-detected environment is, wherein the carrier includes a room, a building or a cavity;

the apparatus for monitoring mold, wherein the apparatus for monitoring mold is used for acquiring mold monitoring data;

a could is used for storing the mold monitoring data; and a management terminal is used for controlling the apparatus for monitoring mold.

In particular, with reference to the FIG. 1, FIG. 1 is the weak current type mold sensor provided by the embodiments of the present application. The mold sensor is the mold detection apparatus of the embodiments of the present application. An operating principle of the mold detection apparatus of the embodiments of the present application includes:

a) if mold spores are included in the air or on the surface of an object, smearing the trophoplasm on the surface of the mold collector 102, wherein the molds grow on the surface of the mold collector 102.

b) surface growth of the molds on the collector will change the electrical properties (for example impedance) of the collector 102.

c) applying a certain voltage to a voltage source 103 by means of a microcurrent detection method, and finally, performing electrical signal treatment to obtain a digital signal 101, wherein whether the molds grow on the surface of the collector or not and the quantity of the molds can be detected.

In some embodiments, the mold collector includes a first collecting unit, a second collecting unit, a third collecting unit and a fourth collecting unit;

the first collecting unit is smeared with the trophoplasm, and the first collecting unit is exposed to air;

the second collecting unit, the third collecting unit, and the fourth collecting unit are used closely;

In some embodiments, the trans-impedance amplifier includes a low-noise operational amplifier unit, a resistor and a capacitor.

In particular, as shown in the FIG. 2, the embodiments of the present application provide a specific mold collector and a circuit structure to achieve the mold sensor.

a) The collector 102 is a solid substrate S1 of some shape (for example, a flat cuboid, a cylinder and the like) and the trophoplasm 202 suitable for growth of the mold 201 is smeared to the collector 102.

b) the substrate of the collector has weak conducting power, i.e., the weak current will be generated by applying a certain voltage V1 to two ends of the collector by the voltage source 103.

c) a weak current is amplified to a voltage signal with a proper amplitude by a trans-impedance amplifier (U1+R1+C1). A specific process is as follows: by means of a characteristic of an input virtual short circuit of U1, an electrode voltage on the left side of S1 is kept in a zero point location. Under the action of the voltage V1, the weak current I flows through S1 and R1 and the voltage V=I*R is generated at the output end of U1. Further, I=V1/RS1, V=V1*R1/RS1, wherein RS1 is equivalent resistance of the S1 collector and RS1 will change weakly along with the quantity of the molds. Thus, the amplitude of the voltage V is measured to reflect the quantity of the molds.

d) the amplified voltage signal V is converted into a digital signal 101 by using an analog-to-digital converter U2.

FIG. 3 is the structural schematic diagram of the mold sensor provided by the embodiments of the present application. As shown in the FIG. 3, the present application provides a specific mold collector and a circuit structure to achieve the mold sensor.

a) The collector S1 is a solid substrate of some shape (for example, a flat cuboid, a cylinder and the like) and the trophoplasm suitable for growth of the mold is smeared to the collector.

b) the substrate of the collector has weak conducting power, i.e., the weak current will be generated by applying a certain voltage V1 to two ends of the collector by the voltage source.

c) there are four collectors: the first collecting unit S1, the second collecting unit S2, the third collecting unit S3 and the fourth collecting unit S4 form the bridge connection as shown in the drawings. Only S1 is exposed to air and the rest three collecting units are used in a closed mode. Growth of molds on the S1 will change the proportion of S2/S4 and S4/S3, which leads to weak voltage change by an output voltage. The weak voltage is amplified to the voltage signal with a proper amplitude by means of instrument amplifiers (U1*a*+U1*b*+R1*a*+R1*b*+R2). A specific process is as follows: change ΔRS1 of RS1 caused by mold growth induces change ΔVin=K*ΔRS1 of a differential voltage output by a bridge, the magnification time of each instrument amplifier is (2R1/R2+1), wherein R1=R1A=R1B, and therefore, the amplified voltage V is equal to K*ΔRS1*(2R1/R2+1).

d) the amplified voltage signal is converted into a digital signal by using an analog-to-digital converter U2.

e) compared with a weak current type method, a weak voltage type method is higher in sensitivity. By adopting a differential signal processing mode, the method has a higher noise inhibiting ability, but is more complex in structure and higher in cost.

FIG. 4 is an interior structure and an equivalent circuit diagram of the mold collector provided by the embodiments of the present application. As shown in the FIG. 4, as the molds are propagated by an air flow, the present application provides two collectors of different structures, wherein (a) and (b) in the FIG. 4 are one-way air flow mold collectors. As grooves coated with the trophoplasm are formed in a direction consistent with the air flow, propagation and growth of the molds in the air flow direction can be detected to the maximum extent. The equivalent circuit is comprised of multiple groups of parallel resistors, and each resistor is comprised of a plurality of small resistors connected in series. Any one resistor changes as the molds growth, which will change the electrical signal intensities output by the collectors. (c) and (d) in the FIG. 4 are air flow mold collectors in any direction. According to a vector superposition principle of analytical geometry, the grooves, vertical to each other, coated with the trophoplasm are used to detect propagation and growth of the molds caused by air flows in any direction. A specific operation is as follows: voltages applied to two ends of the collector are switched periodically, for example, a longitudinal voltage within a t1 time period and a transverse voltage in a t2 time period, electrical signal intensities are measured and recorded separately by means of a same subsequent detection circuit (for example, weak current type and weak voltage type circuits), and then the direction of propagation of the molds in a measured space is calculated according to the vector superposition principle.

Figure 1:
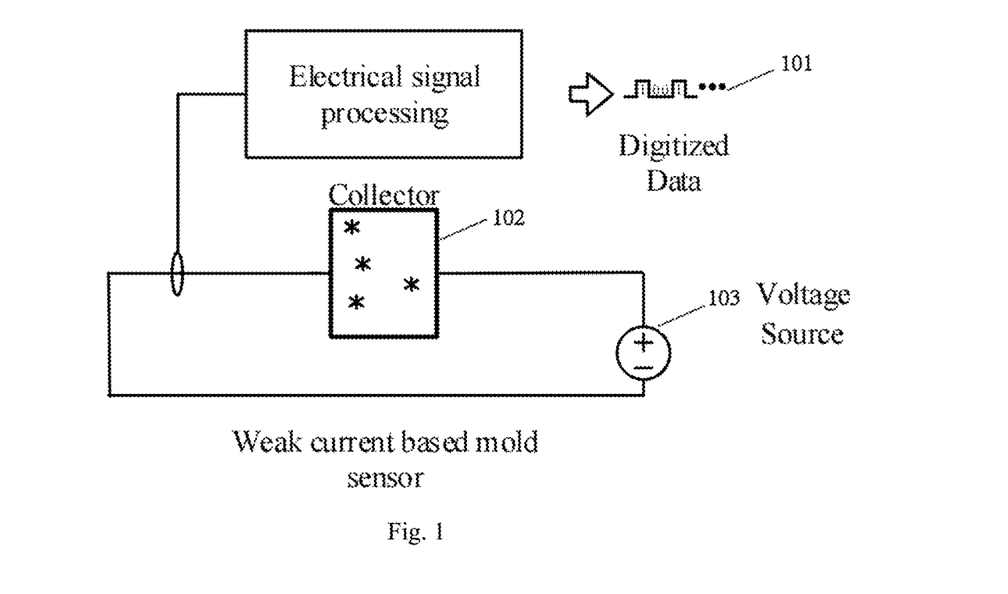
FIG. 1 is the weak current type mold sensor provided by the embodiments of the present application.
Figure 2:
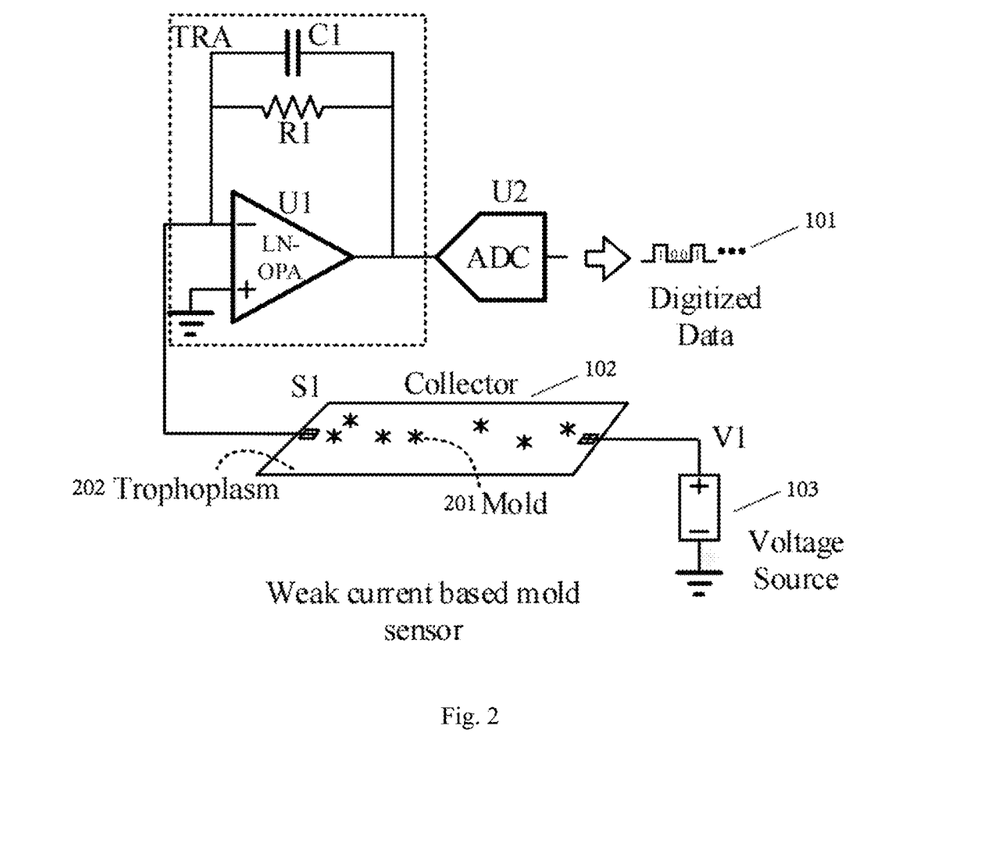
FIG. 2 is a schematic diagram of a circuit philosophy of the mold sensor provided by the embodiments of the present application.
Figure 3:
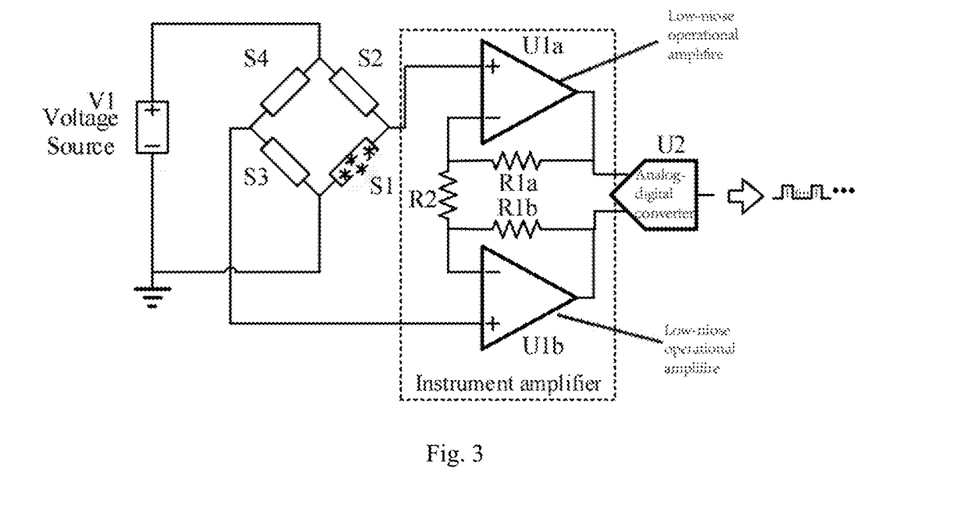
FIG. 3 is a structural schematic diagram of the mold sensor provided by the embodiments of the present application.
Figure 4:
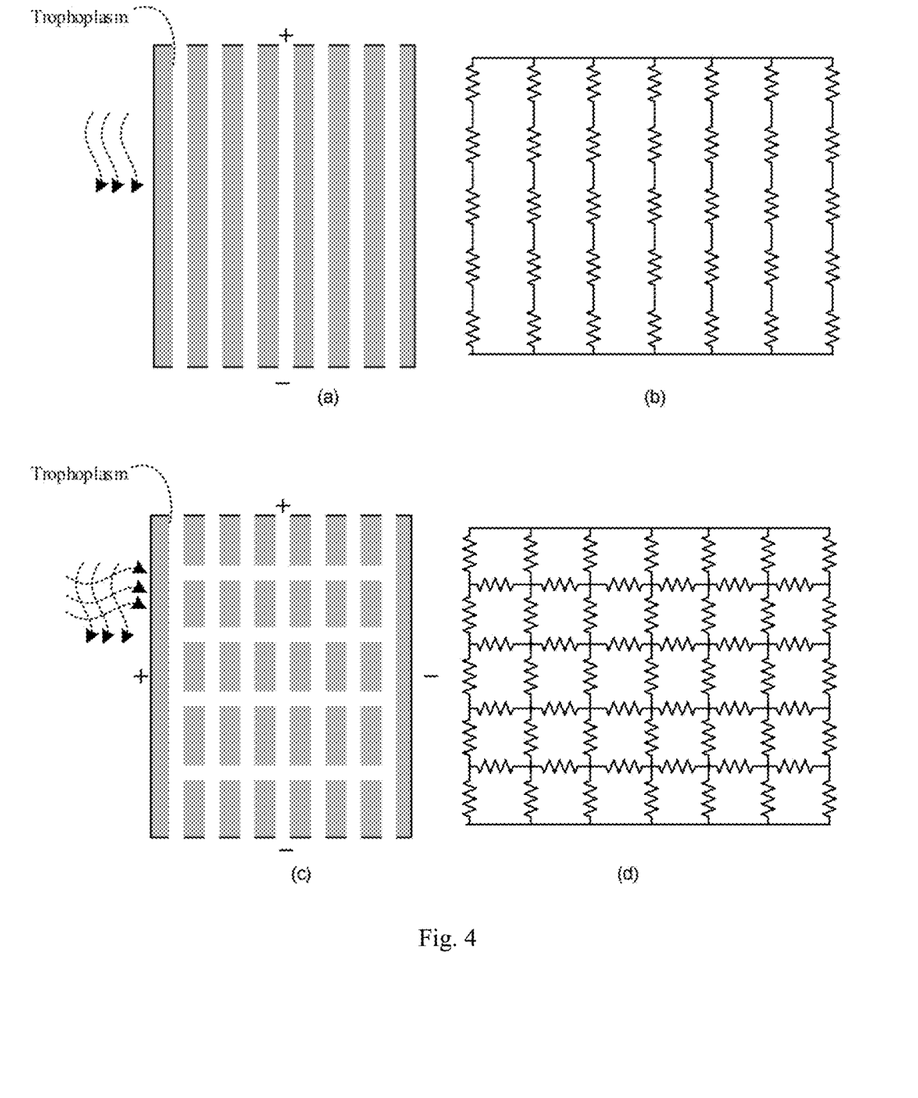
FIG. 4 is an interior structure and an equivalent circuit diagram of the mold collector provided by the embodiments of the present application.
Figure 5:
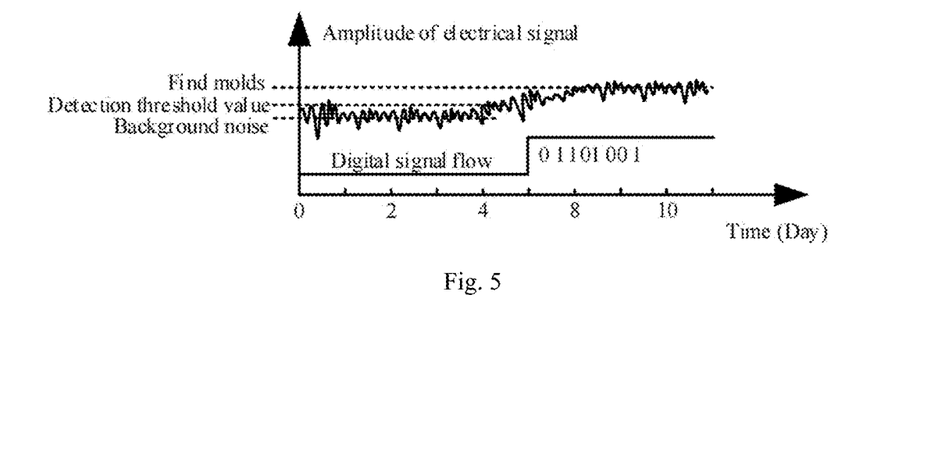
FIG. 5 is a time-varying oscillogram of the analog and digital signals generated by the mold collector provided by the embodiments of the present application.

FIG. 5 is the time-varying oscillogram of the analog and digital signals generated by the mold collector provided by the embodiments of the present application. As shown in the FIG. 5, in order to guarantee the measuring accuracy, a background noise can be sampled and recorded prior to measurement every time. Meanwhile, assume that every data collecting time interval is 1 hour, as the measuring time may be several days, even several months, the collected data is still easily interfered by various environmental factors (reflected by a jittering curve in the figure). These analog electrical signals are digitalized and are handed over to a back-stage microprocessor to judge whether the molds exceed the standard or not accurately after eliminating interference by means of an algorithm.

Figure 6:
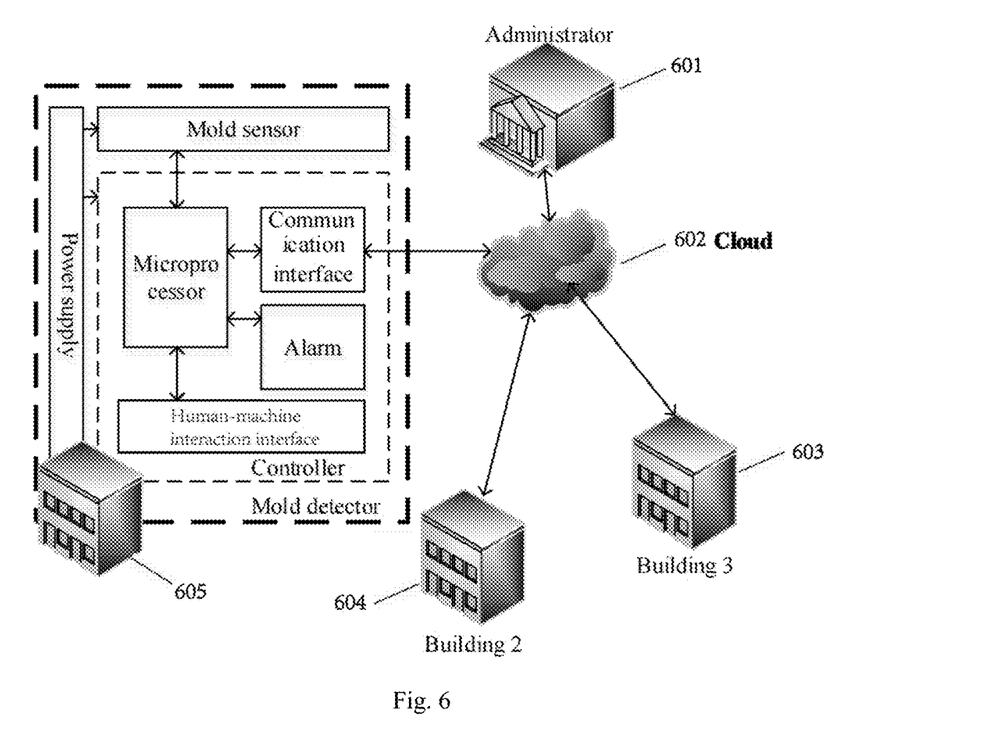
FIG. 6 is a mold detection system, which includes the mold sensor and is combined with a controller, provided by the embodiments of the present application.

FIG. 6 is the mold detection system, which includes the mold sensor and is combined with a controller, provided by the embodiments of the present invention. As shown in the FIG. 6, the invention provides the mold detection system, which includes the mold sensor and is combined with a controller, wherein data sharing is realized by combining the system with a cloud technology. The system includes a first building 605, a second building 604, a third building 603, a cloud terminal 602 and an administrator terminal 601, wherein the first building 605 includes a microprocessor, a communication interface, an alarm and a human-machine interactive interface and the like. The working principle of the system is as follows:

a) The controller includes the microprocessor, the communication interface, the alarm and the human-machine interactive interface and the like and is matched with a proper power supply to supply electricity. Examples below illustrate specific forms which may be implemented by components, and the present invention is not limited to the examples. The microprocessor may be a universal microprocessor such as a single chip microcomputer and a complicated/reduced instruction set central processing unit, the communication interface may be an Internet interface, the alarm may be a light emitting diode indicator lamp, a buzzer and the like, and the power supply may be a direct current power supply (for example, a battery) or an alternating electric supply and the like.

b) the mold sensor transmits the collected standard format digital signal to the microprocessor for analyzing the detection result and judge whether the molds exceed the standard or not, whether alarm is started or not, whether the data is updated to the cloud or not and the like.

c) the detection result and alarm are intervened and processed manually (for example, the molds are eliminated, the alarm is removed, the detector is restarted and the like) by the human-machine interactive interface.

In a word, the embodiments of the present application provide the mold collector which converts the biological information of the molds into the electrical signal, the weak current or voltage detector and the mold controller formed by taking the microprocessor as a center and is combined with the cloud technology. The fundamental principle of the present application is to convert the biological information of the molds into the electrical signal based on microcurrent detection and realizes digitalization, intelligentization and clouding of mold detection by combining an analog and digital signal processing technology with the cloud technology, thereby providing fundamental data and an infrastructure for indoor air quality monitoring of a modern building.

Compared with the prior art, a conventional technical means includes collecting and sending a sample polluted by the molds to a laboratory to culture and proliferate and judging the quantity and types of the molds according to knowledge and experience of professionals by means of microscopic examination. It takes five days to cultivate the polluted sample according to the mold detection method of national standard GB4789.14-94. mold detection paper has been applied in food detection field since 1998, and the cultivation time has been shortened to 40-48 hours. These conventional means cannot be used for finding excess molds in time in the living environment and requires complex laboratory equipment, instruments and professional knowledge reserve, which is not suitable for being popularized and commercialized.

In comparison, as the electrical means is adopted to detect molds, the present application has the advantages of low cost, high precision, miniaturization, full automation and the like and can be combined with more advanced microprocessors, communication interfaces and cloud technologies, such that the actual application space and the economic value of the present application are expanded greatly.

In the description, description with reference to "one embodiment", "some embodiments", "exemplary embodiments", "specific exemplary embodiments" or "some exemplary embodiments" and the like means specific features, structures, materials or characteristics described in combination with the embodiments or the exemplary embodiments are included in at least one embodiment or the exemplary embodiment of the present application. In the description, schematic expressions of the terms do not have to mean same embodiments or exemplary embodiments. Furthermore, specific features, structures, materials or characteristics described can be combined in any one or more embodiments or exemplary embodiments in proper manners.

Although the embodiments of the present application have been shown and described, those skilled in the art can understand that various changes, modifications, substitutions, and alterations could be made hereto without departing from the spirit and purpose of the present application. The scope of the present application is limited by the claims and the equivalents hereof.

Although the preferred embodiments of the present application are described in detail, the application is not limited to the embodiments. Those skilled in the art further could make various equivalent deformations or substitutions without violating the spirit of the present application, and these equivalent deformations or substitutions are included in the scope defined by the claims of the disclosure.

The invention claimed is:

1. An apparatus for detecting mold based on electrical signals, comprising:
a mold collector includes a layer of material for growing mold, and an electrically conductive substrate;
wherein the mold collector includes a first collecting unit, a second collecting unit, a third collecting unit, and a fourth collecting unit;

wherein the first collecting unit includes the layer of material for growing mold, and the first collecting unit is exposed to air;

wherein the second collecting unit, the third collecting unit, and the fourth collecting unit are sealed without exposure to air; and wherein the first collecting unit, the second collecting unit, the third collecting unit and the fourth collecting unit form a closed loop connection;

a power supply configured to supply a voltage to the substrate of the mold collector to generate a current from the substrate of the mold collector;

a trans-impedance amplifier configured to amplify the current generated from the substrate of the mold collector to a voltage signal;

wherein the trans-impedance amplifier comprises a low-noise operational amplifying unit, a resistor, and a capacitor;

an analog-to-digital converter configured to convert the voltage signal amplified by the trans-impedance amplifier into a digital signal for determining a quantity of molds;

wherein the mold collector is a unidirectional air flow mold collector configured to provide a unidirectional air flow, wherein the unidirectional air flow mold collector includes multiple parallel grooves smeared with the material for growing mold, and wherein the multiple parallel grooves are formed in a direction from a first collector end that receives a high voltage to a second collector end that receives a low voltage;

a controller configured to analyze collected signals and detect a specific result;

wherein the controller comprises a microprocessor, a communication interface, an alarm, and a human-machine interactive interface;

a background noise detector configured to acquire environmental and apparatus noise levels.

* * * * *